United States Patent [19]

Lagrange et al.

[11] Patent Number: 5,717,108
[45] Date of Patent: Feb. 10, 1998

[54] PROCESS FOR THE PREPARATION OF INDOLE COMPOUNDS

[75] Inventors: Alain Lagrange, Coupvray; Michel Philippe, Wissous; Rémy Tuloup, Miniac Sous Becherel, all of France

[73] Assignee: L'Oreal, Paris, France

[21] Appl. No.: 759,648

[22] Filed: Dec. 5, 1996

[30] Foreign Application Priority Data

Dec. 6, 1995 [FR] France ............... 95 14373

[51] Int. Cl.$^6$ ............... C07D 209/12
[52] U.S. Cl. ............... 548/483; 548/484; 548/485; 548/486; 548/490; 548/491
[58] Field of Search ............... 548/483, 484, 548/485, 486, 490, 491

[56] References Cited

U.S. PATENT DOCUMENTS

| | | | |
|---|---|---|---|
| 5,135,544 | 8/1992 | Grollier et al. | 8/405 |
| 5,391,482 | 2/1995 | Mangold | 435/18 |

FOREIGN PATENT DOCUMENTS

| | | |
|---|---|---|
| A-0682014 | 11/1995 | European Pat. Off. |
| A-2649009 | 4/1991 | France . |
| A-981192 | 1/1965 | United Kingdom . |
| WO-A-9503421 | 2/1995 | WIPO . |

*Primary Examiner*—Joseph McKane
*Attorney, Agent, or Firm*—Finnegan, Henderson, Farabow, Garrett & Dunner, L.L.P.

[57] ABSTRACT

The present invention relates to a novel process for the preparation of a monohydroxyindole or dihydroxyindole compound by a single step of placing in contact, in a solvent medium, at least one hydrolase with at least one indole compound bearing one or two radicals connected by an ester function to the benzene ring.

20 Claims, No Drawings

PROCESS FOR THE PREPARATION OF INDOLE COMPOUNDS

The present invention relates to a novel process for the enzymatic preparation of indole compounds.

Indole and its derivatives are starting materials widely used in the dyestuffs, cosmetic, pharmaceutical and food industries. Indole is, in particular, one of the starting materials which can be used for the synthesis of tryptophan, which is an essential amino acid in nutrition.

Indoles are generally synthesized in several long and expensive steps. Furthermore, these synthesises require vigorous oxidation steps, at high reaction temperatures, often above 140° C., thereby entailing handling risks.

Consequently, various processes have been proposed for the preparation of indole compounds. For example, it has been proposed to prepare indole compounds by catalytic hydrogenation under pressure or by hydrogen transfer as described in French patent application FR-A-2,606,405. An alternative process for the preparation of indole compounds is catalytic reductive cyclization as described, for example, in U.S. Pat. No. 4,595,765.

These processes require the use of indole precursors bearing groups that are compatible with a hydrogenation reaction, which results in a complication of the process in the preceding steps. Furthermore, these processes generally lead to the production of by-products which affect the purity of the reaction.

It has also been proposed to prepare indole compounds by dehydrogenation of indole derivatives, as described, for example, in German patent application DE-A-4,204,089. An alternative process is basic hydrolysis starting with indole 5,6-diacetate, as described, for example, by R. J. S. Beer et al. in the Journal of the Chemical Society, 2223–2226, 1948.

The drawback of these last two methods is that the reaction preferably takes place in water in the presence of an alkaline agent, which generally results in rapid degradation of the indole compound obtained.

It is while searching to overcome these problems that the inventors have discovered the process which forms the subject of the present invention.

The subject of the present invention is thus a novel process for the preparation of indole compounds in a single step comprising placing in contact, in a solvent medium, at least one hydrolase with at least one indole compound bearing one or two radicals connected by an ester function to the benzene ring, thereby obtaining a mono- or a dihydroxyindole.

According to this process, no by-product is formed, this being an advantage both from the point of view of the purity of the final product obtained and from the point of view of the reaction yield of this product. Furthermore, this simple synthetic process does not require the use of an alkaline agent in the solvent medium, thereby avoiding the rapid degradation of the indole compound obtained.

According to the process in accordance with the invention, the starting indole compounds bearing one or two radicals connected by an ester function to the benzene ring are preferably selected from the compounds of formula (I) below:

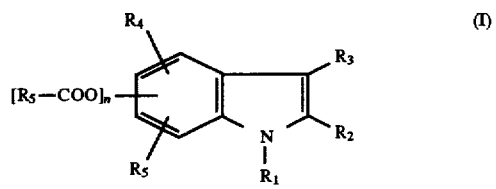

in which:

n is an integer equal to 1 or 2;

$R_1$ represents a hydrogen atom or a $(C_1-C_4)$ alkyl radical;

$R_2$, $R_3$, $R_4$ and $R_6$, which may be identical or different, represent a hydrogen atom, a $(C_1-C_8)$ alkyl radical, a $(C_1-C_4)$alkoxy$(C_1-C_4)$alkyl radical, a $(C_1-C_8)$alkoxy radical, a $(C_1-C_4)$alkoxy$(C_1-C_4)$alkoxy radical, a $(C_5-C_{10})$ aryl radical, a $(C_5-C_{10})$aryloxy radical, a $(C_5-C_{10})$aryl radical containing from 1 to 3 hetero atoms, such as an oxygen or nitrogen atom, a $(C_5-C_{10})$ aryloxy radical containing from 1 to 3 hetero atoms, such as an oxygen or nitrogen atom, a $(C_1-C_8)$ acyl radical or alternatively a radical selected from the following radicals:

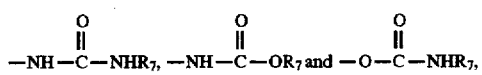

in which the radical $R_7$ represents a $C_1-C_8$ alkyl radical;

$R_5$ represents a $(C_1-C_8)$alkyl radical, a $(C_5-C_{10})$aryl radical, a $(C_5-C_{10})$aryl$(C_1-C_8)$alkyl radical, a $(C_1-C_8)$alkyl $(C_5-C_{10})$aryl radical or a $(C_2-C_8)$aryl-$(C_5-C_{10})$aryl radical.

In the above formula (I), the alkyl and alkoxy radicals may be linear or branched, and saturated or unsaturated.

The acyl radical preferably represents an alkanoyl radical derived from an aliphatic carboxylic acid having from 5 to 10 carbon atoms, such as, for example, formyl, acetyl, etc. groups; or an aroyl group derived from an aromatic carboxylic acid, such as the benzoyl group.

The mono- and dihydroxyindoles which may be obtained by the process in accordance with the invention, correspond to formula (11) below:

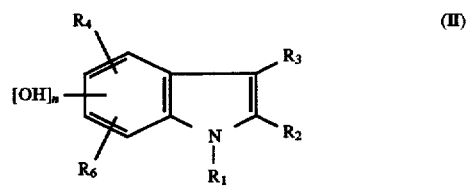

in which:

n is an integer equal to 1 or 2;

and $R_1$, $R_2$, $R_3$, $R_4$ and $R_6$ have the same meanings as in formula (I).

Among the indole compounds which may be obtained using the process of the invention, mention may preferably be made of:

5,6-dihydroxyindole,
6-hydroxyindole,
4-hydroxyindole,
5-hydroxyindole,
7-hydroxyindole,
5,7-dihydroxyindole.

Particularly preferred compounds are:

5,6-dihydroxyindole,
6-hydroxyindole,
4-hydroxyindole,
7-hydroxyindole.

3

According to the process of the invention, the nature of the hydrolase is not critical. The term hydrolase is understood to refer to any enzymatic substance which, under the action of water, leads to the cleavage of an ester bond. These hydrolases are described, for example, by H. G. Davis, R. H. Green, D. R. Kelly and S. M. Roberts in "Biotransformations in preparative organic chemistry", Academic Press, 1989, the disclosure of which is incorporated herein by reference.

Among the hydrolases which can be used according to the invention, mention may be preferably made in particular of lipases, esterases and proteases. These hydrolases may optionally be bound to, i.e., supported on, inert supports such as glass beads, Celite, clay or resin.

With respect to the lipase, mention may preferably be made most particularly of the lipase from Pseudomonas fluorescens and the lipase from Candida Antartica bound to resin and marketed under the name Novozym 435 by the company Novo-Nordisk.

According to the process of the invention, the hydrolase or hydrolases preferably represent approximately from 5% to 500% by weight relative to the weight of the starting indole compound to be reacted, and even more preferably approximately from 10% to 100% by weight relative to the weight of the starting indole compound.

According to a preferred embodiment of the process according to the invention, the pH of the solvent medium is approximately from 5 to 9 and even more preferably is approximately from 6.5 to 7.5.

In order to avoid variations in pH during the reaction, a standard buffer solution such as, for example, phosphate buffer is preferably added to the solvent medium.

The solvent used is advantageously an inert solvent such as, for example, a $C_1$–$C_4$ lower alcohol such as methanol, ethanol or isopropanol; acetonitrile; tetrahydrofuran; toluene; hexane; heptane, chloroform or dichloromethane, in the presence or absence of a phase transfer agent such as, for example, a quarternary ammonium or a sulphosuccinic acid salt. The solvent used is preferably a $C_1$–$C_4$ alcohol such as ethanol.

According to the invention, the reaction temperature is not critical but this temperature should be compatible with correct functioning of the enzyme used.

According to an advantageous embodiment of the process of the invention, the reaction temperature is approximately from 20° to 80° C. and preferably is approximately from 25° to 50° C. A temperature most particularly preferred is one of about 37° C.

When the reaction is complete, the expected products such as, for example, the 5,6-dihydroxyindole, may, if necessary, be recovered by methods that are well known in the state of the art, such as filtration or crystallization.

The indole compounds obtained according to the process in accordance with the invention may also subsequently be purified according to standard methods that are well known to those skilled in the art, such as, for example, chromatography on silica gel.

The indole products obtained according to the process in accordance with the invention may be used for many purposes, for example as intermediates for preparing amino acids, tryptamine alkaloids, etc. Alternatively the indole products may be used as finished products in any type of chemical, cosmetic, food or pharmaceutical industry or the like.

The preparation examples which follow are intended to illustrate the invention without, however, limiting the scope thereof.

4

EXAMPLES

EXAMPLE 1: Synthesis of 5,6-dihydroxyindole 6 g of 5,6-diacetoxyindole, 4 g of Novozym 435 marketed by the company Novo-Nordisk (hydrolase), 100 ml of 95° ethanol and 100 ml of 0.1 M phosphate buffer at pH 7 were mixed together in a 500 ml conical flask.

After stirring for 2 hours 30 minutes at a temperature of about 37° C., the reaction mixture was filtered, evaporated to dryness and then taken up in 50 ml of ethyl acetate.

The solution obtained was then chromatographed on silica gel, under nitrogen pressure, using an ethyl acetate/heptane mixture (20/80) as eluent.

After removal of the unreacted 5,6-diacetoxyindole, the expected product was recovered, the elemental analysis of which for $C_8H_7NO_2$ was as follows:

|  | % | | | |
| --- | --- | --- | --- | --- |
|  | C | H | N | O |
| Calculated | 64.43 | 4.70 | 9.39 | 21.47 |
| Found | 64.18 | 4.89 | 9.22 | 21.46 |

What is claimed is:

1. A process for the preparation of a monohydroxyindole or dihydroxyindole compound in a single step, said process comprising the steps of placing at least one hydrolase in contact with at least one indole compound bearing one or two R groups connected by an ester function to the benzene ring, wherein said process is carried out in a solvent medium.

2. A process according to claim 1, wherein said at least one indole compound bearing one or two R groups connected by an ester function to the benzene ring is selected from compounds of formula (I):

wherein:

n is an integer equal to 1 or 2;

$R_1$ represents a hydrogen atom or a ($C_1$–$C_4$)alkyl;

$R_2$, $R_3$, $R_4$ and $R_6$, which may be identical or different, represent a hydrogen atom, a ($C_1$–$C_8$)alkyl, a ($C_1$–$C_4$) alkoxy($C_1$–$C_4$)alkyl, a ($C_1$–$C_8$)alkoxy, a ($C_1$–$C_4$) alkoxy($C_1$–$C_4$)alkoxy, a ($C_5$–$C_{10}$) aryl, a ($C_5$–$C_{10}$) aryloxy, a ($C_5$–$C_{10}$)aryl containing from 1 to 3 hetero atoms, a ($C_5$–$C_{10}$)aryloxy containing from 1 to 3 heteroatoms, a ($C_1$–$C_8$)acyl or, alternatively, a selected from the following:

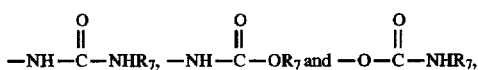

wherein $R_7$ represents a $(C_1-C_8)$ alkyl;

$R_5$ represents a $(C_1-C_8)$alkyl, a $(C_5-C_{10})$ aryl, a $C_5-C_{10}$ aryl$(C_1-C_8)$alkyl, a $(C_1-C_8)$alkyl$(C_5-C_{10})$aryl or a $(C_2-C_8)$acyl- $(C_5-C_{10}$aryl.

3. A process according to claim 2, wherein said hetero atom is oxygen or nitrogen.

4. A process according to claim 2, wherein, in formula (I), said alkyl and alkoxy are linear or branched, and saturated or unsaturated and further wherein said acyl denotes an alkanoyl derived from an aliphatic carboxylic acid having from 5 to 10 carbon atoms or an aroyl group derived from an aromatic carboxylic acid.

5. A process according to claim 1, wherein said monohydroxyindole or dihydroxyindole compound is of the formula (II) below:

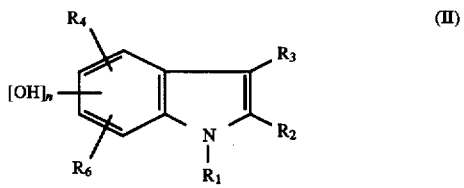

wherein:

n is an integer equal to 1 or 2;

$R_1$ represents a hydrogen atom or a $(C_1-C_4)$ alkyl;

$R_2$, $R_3$, $R_4$ and $R_6$, which may be identical or different, represent a hydrogen atom, a $(C_1-C_8)$alkyl, a $(C_1-C_4)$ alkoxy$(C_1-C_4)$alkyl, a $(C_1-C_8)$alkoxy, a $(C_1-C_4)$ alkoxy$(C_1-C_4)$alkoxy, a $(C_5-C_{10})$ aryl, a $(C_5-C_{10})$ aryloxy, a $(C_5-C_{10})$ aryl containing from 1 to 3 hetero atoms, a $(C_5-C_{10})$ aryloxy containing from 1 to 3 hetero atoms, a $(C_1-C_8)$ acyl or alternatively selected from the following:

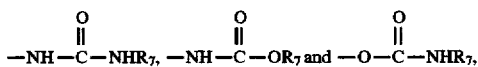

in which $R_7$ represents a $(C_1-C_8)$ alkyl.

6. A process according to claim 5, wherein said hetero atom is nitrogen or oxygen.

7. A process according to claim 1, wherein said monohydroxyindole or dihydroxyindole compound is selected from 5,6-dihydroxyindole, 6-hydroxyindole, 4-hydroxyindole, 5-hydroxyindole, 7-hydroxyindole and 5,7-dihydroxyindole.

8. A process according to claim 1, wherein said at least one hydrolase is selected from lipases, esterases and proteases.

9. A process according to claim 8, wherein said at least one hydrolase is bound to an inert support.

10. A process according to claim 9, wherein said inert support is selected from glass beads, Celite, clay and resin.

11. A process according to claim 8, wherein said at least one hydrolase is selected from the lipase from Pseudomonas fluorescens and the lipase from Candida Antartica bound to resin.

12. A process according to claim 1, wherein said at least one hydrolase represents from 5% to 500% by weight relative to the weight of the starting indole compound to be reacted.

13. A process according to claim 12, wherein said at least one hydrolase represents from 10% to 100% by weight relative to the weight of the starting indole compound to be reacted.

14. A process according to claim 1, wherein said solvent medium has a pH ranging from 5 to 9.

15. A process according to claim 14, wherein said solvent medium has a pH ranging from 6.5 to 7.5.

16. A process according to claim 14, wherein said solvent medium contains a buffer solution.

17. A process according to claim 1, wherein the solvent of said solvent medium is an inert solvent selected from $C_1-C_4$ alcohols, acetonitrile, tetrahydrofuran, toluene, hexane, heptane, chloroform and dichloromethane.

18. A process according to claim 17, wherein the solvent of said solvent medium is a $C_1-C_4$ alcohol.

19. A process according to claim 1, wherein said process has a reaction temperature ranging from 20° to 80° C.

20. A process according to claim 19, wherein said reaction temperature ranges from 25° to 50° C.

* * * * *

UNITED STATES PATENT AND TRADEMARK OFFICE
CERTIFICATE OF CORRECTION

PATENT NO. : 5,717,108
DATED : March 16, 1998
INVENTOR(S) : Lagrange et al.

It is certified that error appears in the above-indentified patent and that said Letters Patent is hereby corrected as shown below:

Column 4, line 66, "heteroatoms" should read --hetero atoms--; and before "selected" delete "a".

In Claim 2, col. 5, line 7, "a$C_5$-$C_{10}$)" should read --a ($C_5$-$C_{10}$)--.

In Claim 2, col. 5, line 9, "($C_2$-$C_8$acyl- ($C_5$-$C_{10}$aryl." should read --($C_2$-$C_8$)acyl-($C_5$-$C_{10}$)aryl.--.

Signed and Sealed this

Twenty-eighth Day of July, 1998

Attest:

BRUCE LEHMAN

*Attesting Officer*  *Commissioner of Patents and Trademarks*

UNITED STATES PATENT AND TRADEMARK OFFICE
CERTIFICATE OF CORRECTION

PATENT NO. : 5,717,108
DATED : February 10, 1998
INVENTOR(S) : LAGRANGE et al.

Page 1 of 2

It is certified that error appears in the above-identified patent and that said Letters Patent is hereby corrected as shown below:

At column 2, line 1, in the formula:

This: " 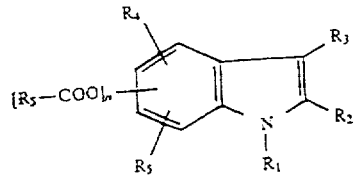 (I) "

should read:

-- 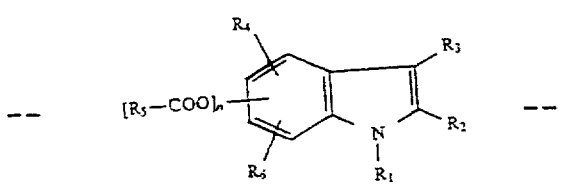 (I) --

UNITED STATES PATENT AND TRADEMARK OFFICE
CERTIFICATE OF CORRECTION

PATENT NO. : 5,717,108
DATED : February 10, 1998
INVENTOR(S) : LAGRANGE et al.

Page 2 of 2

It is certified that error appears in the above-identified patent and that said Letters Patent is hereby corrected as shown below:

At column 4, in claim 2, " 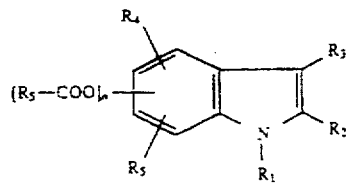 (I) "

This: = should read-

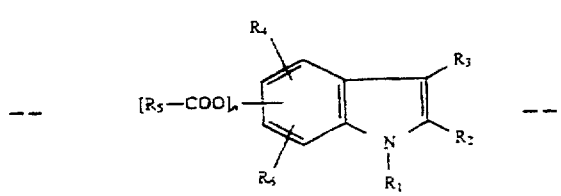 (I)
-- --

Signed and Sealed this

First Day of September, 1998

Attest:

BRUCE LEHMAN

Attesting Officer

Commissioner of Patents and Trademarks